United States Patent
Scholz et al.

(10) Patent No.: US 8,231,769 B2
(45) Date of Patent: Jul. 31, 2012

(54) ELECTRODE AND SINGLE-ROD MEASURING CHAIN FOR DETERMINING ELECTROCHEMICAL POTENTIALS

(75) Inventors: Katrin Scholz, Bobritzsch (DE); Reiner Franzheld, Waldheim (DE); Ingrid Wunderlich, Radebeul (DE)

(73) Assignee: Endress + Hauser Conducta Gesellschaft fur Mess- u. Regeltechnik mbH + Co. KG, Gerlingen (DE)

( * ) Notice: Subject to any disclaimer, the term of this patent is extended or adjusted under 35 U.S.C. 154(b) by 323 days.

(21) Appl. No.: 12/312,638

(22) PCT Filed: Nov. 15, 2007

(86) PCT No.: PCT/EP2007/062399
§ 371 (c)(1),
(2), (4) Date: Jan. 25, 2010

(87) PCT Pub. No.: WO2008/061934
PCT Pub. Date: May 29, 2008

(65) Prior Publication Data
US 2010/0126850 A1   May 27, 2010

(30) Foreign Application Priority Data

Nov. 21, 2006   (DE) .......................... 10 2006 055 221

(51) Int. Cl.
*G01N 27/333* (2006.01)
*G01N 27/36* (2006.01)
*G01N 27/401* (2006.01)
(52) U.S. Cl. .......................... 204/420; 204/433; 204/435
(58) Field of Classification Search .................. 204/433, 204/435, 420
See application file for complete search history.

(56) References Cited

U.S. PATENT DOCUMENTS

| | | | |
|---|---|---|---|
| 3,676,319 A | 7/1972 | Kirsten | |
| 4,162,211 A | 7/1979 | Jerrold-Jones | |
| 4,913,793 A * | 4/1990 | Leonard | 204/433 |
| 7,196,524 B2 * | 3/2007 | Wittmer et al. | 324/458 |
| 7,276,142 B2 * | 10/2007 | West et al. | 204/433 |
| 7,704,359 B2 * | 4/2010 | Sovrano et al. | 204/435 |
| 2003/0150726 A1 * | 8/2003 | West et al. | 204/433 |

FOREIGN PATENT DOCUMENTS

| | | |
|---|---|---|
| DE | 36 17 479 A1 | 11/1987 |
| DE | 37 04714 A1 | 8/1988 |
| DE | 89 12 731.5 | 3/1990 |
| DE | 39 42 500 A1 | 6/1991 |
| DE | 100 18 750 A1 | 1/2001 |
| DE | 103 54 100 A1 | 6/2005 |
| EP | 1 172 648 A1 | 1/2002 |

* cited by examiner

*Primary Examiner* — Bruce Bell
(74) *Attorney, Agent, or Firm* — Bacon & Thomas, PLLC

(57) ABSTRACT

An electrode comprising: a least a first, preferably cylindrical, glass body, in which at least a first chamber is formed; at least a first electrolyte, which is located in the first chamber; at least a first potential-forming element, which is arranged in the chamber, and forms a first potential when contacted by the first electrolyte; at least a first closing element, which is axially fixed in the first chamber for enclosing the first electrolyte and the first potential-forming element and sealedly closes the first chamber; wherein, additionally, the first closing element is conductive, the first potential-forming element conductingly contacts the first closing element, and the electrode furthermore includes at least a first electrical conductor, which electrically contacts the first closing element on the side of the first closing element facing away from the first electrolyte.

19 Claims, 3 Drawing Sheets

ELECTRODE AND SINGLE-ROD MEASURING CHAIN FOR DETERMINING ELECTROCHEMICAL POTENTIALS

TECHNICAL FIELD

The present invention relates to an electrode, especially a glass electrode, and to a single-rod measuring chain for determining electrochemical potentials, for example, the pH-dependent potential. Glass electrodes find wide application in the above field of application. For the measuring of pH, especially, so called single-rod measuring chains are applied having a pH glass-half-cell, or pH-electrode, and a reference half-cell, or reference electrode, which provides a constant reference potential. For forming the reference potential, primarily an Ag/AgCl-body in a KCl-solution of constant concentration is used.

BACKGROUND DISCUSSION

Conventional single-rod measuring chains include, essentially, two concentric glass cylinders, which are joined together at a first axial end section by melting, wherein the inner cylinder has at the first end section, usually, a pH glass-membrane and is filled with a buffer, the annular chamber between the inner and the outer cylinder contains the KCl-solution, and the outer cylinder has in the first axial end section or in a section axially adjoining such, a porous diaphragm, through which an electrolyte bridge to the surrounding, measured medium is produced. Both from the inner cylinder as well as from the annular chamber, metal conductors extend, for providing access to, respectively, the pH-potential and the reference potential.

A structural requirement is to provide sealed closure of the annular chamber and the inner cylinder at a second axial end section lying opposite to the first axial end section, without interfering with the accessing of the potentials. The sealing of the closure must, in such case, be assured, both at high temperatures, for example, >130° C. during autoclaving, as well as also at high pressures, for example, up to about 16 bar or more.

Conventionally, wires, as metal conductors, are bonded into glass for sealing, by melting of the glass, or they are held adhesively by potting in feed-throughs in more or less suitable materials. These feed-throughs leave the manufacturing process successfully sealed only after the expenditure of considerable effort.

SUMMARY OF THE INVENTION

An object of the invention is, consequently, to provide potentiometric electrodes overcoming the disadvantages of the state of the art.

The object is achieved according to the invention by an electrode including: at least a first glass body, in which at least a first chamber is formed; at least a first electrolyte, which is located in the first chamber; at least a first potential-forming element, which is arranged in the chamber and forms a first potential when contacted by the first electrolyte; at least a first closing element, which is axially fixed in the first chamber for enclosing the first electrolyte and the first potential-forming element, and which sealedly closes the first chamber; characterized in that the first closing element is conductive, the first potential-forming element conductively contacts the first closing element, and the electrode further includes at least a first electrical conductor, which electrically contacts the first closing element on a side of the first closing element facing away from the first electrolyte.

The electrode of the invention can be a single pH-electrode or a single reference electrode. Equally, the pH-electrode and/or the reference electrode of a single-rod measuring chain can be embodied as an electrode of the invention.

In a first embodiment of the invention, the electrode is a pH-electrode.

The first glass body can, according to the first embodiment of the invention, comprise, for example, a cylindrical tube, whose first axial end is closed with a pH glass-membrane to form the first chamber. The first electrolyte comprises a pH-buffer, which can contain, for example, KCl.

The first potential-forming element comprises, then, for example, an AgCl-reservoir, which is wetted by the electrolyte, or pH-buffer, and is in electrically conducting connection with the electrically conductive, closing element.

In a currently preferred embodiment, the potential-forming element comprises a conductive element body, which is composed of a porous, especially open-pored, elastomer, whose pores contain the electrolyte, or pH-buffer, and AgCl, and which is in electrical contact with the closing element. Embedded in the elastomer are, for example, silver particles, silver-containing particles, or glass particles coated with Ag, in order to provide the body with a sufficient electrical conductivity.

The closing element can, in a first further development, comprise a conductive closing body, which is composed of an elastomer, in which, likewise, the cited particles with silver-containing surfaces are embedded, in order to make the body electrically conductive. The closing body can, for example, be pressed from the second axial end of the cylindrical glass body into the opening of the glass body, in order to close the opening. The closing element is in such case held sufficiently in its axial position by friction arising from radial forces exerted by it against the inner wall of the cylindrical glass body. The closing body can, depending on embodiment of the pH electrode, be a solid stopper, or an annular body, or O-ring.

An O-ring is required, when a temperature probe is arranged in the cylindrical glass body, with the temperature probe extending from the second end section of the cylindrical glass body in the direction of the pH glass-membrane.

In a further development of the invention, the element body is formed as one-piece with the closing body.

In another embodiment of the invention, the closing element comprises an adhesive, which is made conductive by the embedding of silver particles, silver-containing particles, or silver-coated, glass particles therein.

Suitable elastomers, or sealing compounds, especially silicone compounds with silver additives, or silver-containing additives, for achieving the required conductivity are obtainable, for example, from Laird-Technologies, Rosenheim, Germany.

The principles of the above embodiments of the electrode of the invention can be transferred correspondingly to reference half-cells. In such case, instead of the pH glass-membrane in a first end section of the cylindrical glass body, a porous diaphragm is provided for implementing the corresponding junction. The electrolyte comprises a reference electrolyte corresponding to the desired function, for example, a 3 molar KCl-solution.

Equally, the above explanations hold for a so called single-rod measuring chain, which comprises a pH-electrode and a coaxially arranged, reference electrode, wherein the cylindrical glass body of the reference electrode surrounds the cylindrical glass body of the pH-electrode to form an annular chamber, wherein the annular chamber is closed in the region of the first end section, for example, by melting the two glass bodies to join them together. A reference electrolyte and an element forming a reference potential are arranged in the annular chamber. At least one of the chambers, thus the chamber of the pH-electrode or the annular chamber of the second electrode is closed with an above described, conductive, closing body. Preferably, however, both chambers are closed with one of the above described, conductive, closing bodies.

BRIEF DESCRIPTION OF THE DRAWINGS

The invention will now be explained on the basis of the examples of embodiments presented in the drawing, the figures of which show as follows.

DETAILED DISCUSSION IN CONJUNCTION WITH THE DRAWINGS

Figure 1:
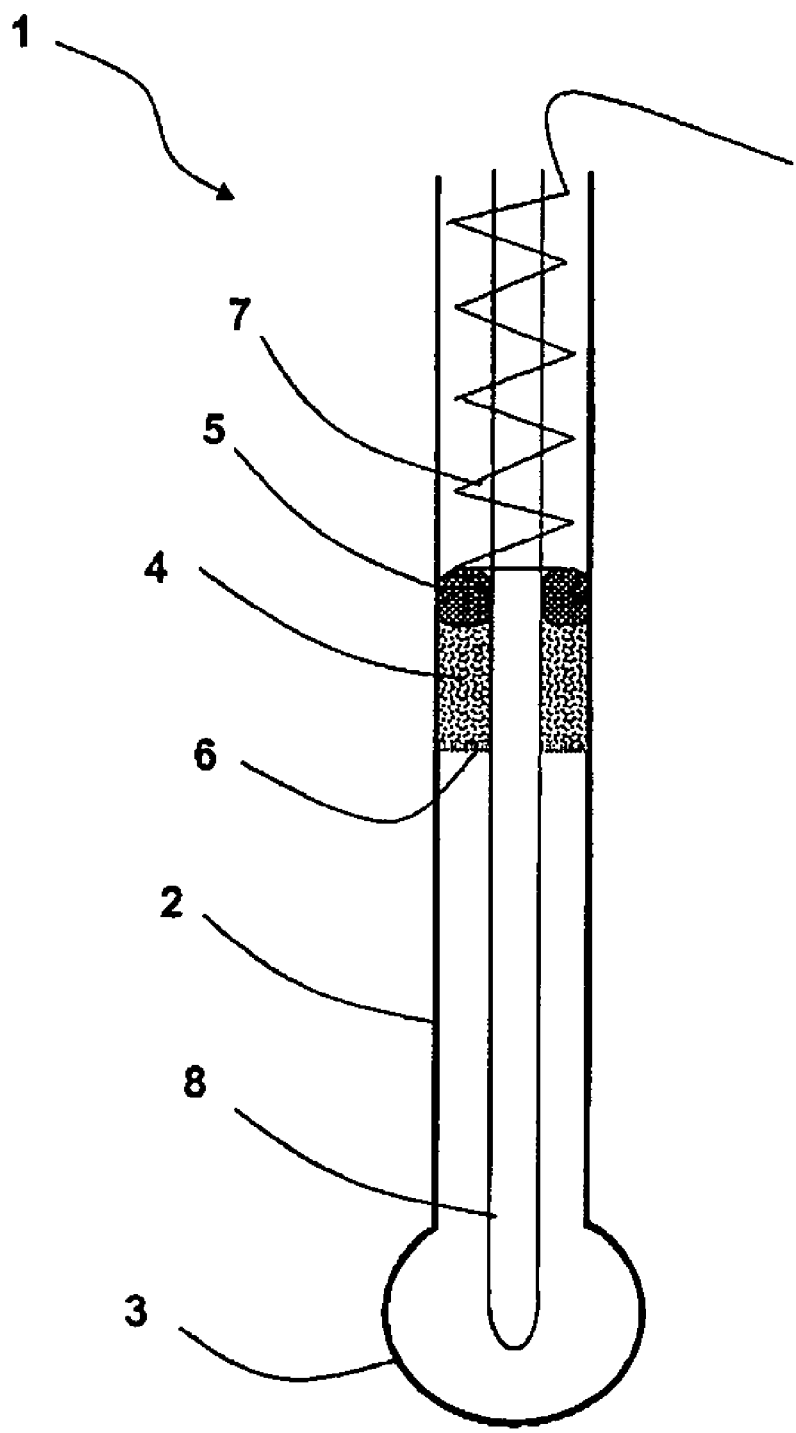
FIG. 1 a longitudinal section through a first example of an embodiment of a pH-electrode of the invention.

The pH-electrode 1 shown in FIG. 1 includes a cylindrical glass tube 2, whose lower end is closed with a pH glass-membrane 3. The glass tube 2 and the pH glass-membrane 3 enclose a volume, which is filled with a KCl-containing pH-buffer.

For forming a pH-dependent potential, an AgCl-reservoir 4 is provided, which comprises silver grains, or grains with a silver surface, which are, at least partially, chlorided. The AgCl-reservoir is in electrically conducting contact with a closing element 5, which closes the glass tube 2. For fixing the axial position of the AgCl-reservoir 4, there is provided in the glass tube 2 an axial barrier 6, which is porous for the pH-buffer, so that such can wet the AgCl-reservoir. The barrier 6 can comprise, for example, an annular sieve plate of glass or plastic.

The closing element 5 comprises, in this embodiment, an electrically conductive O-ring, which is manufactured of an elastomer containing silver particles. The O-ring is held sufficiently against movement in the axial direction by radial forces providing frictional engagement.

For providing access to the pH-dependent potential, the O-ring is contacted via a contact spring 7, which presses against the side of the O-ring facing away from the AgCl-reservoir. The contact spring is sufficiently axially pre-compressed, that an electrical contact remains in the presence of shaking and temperature fluctuations. However, the pre-compression of the contact spring is not so great as to cause axial shifting of the O-ring.

Extending along the axis of the pH-electrode is the glass shaft of a temperature sensor 8, which registers temperature of the pH-buffer about in the center of the volume enclosed by the pH glass-membrane. Due to the presence of this temperature sensor, the closing element 5 and the axial barrier 6 are embodied to be ring-shaped. When the temperature sensor is absent, the closing element 5 and the axial barrier 6 are correspondingly embodied, respectively, as solid stopper (or plug) and traversing sieve plate.

Figure 2:
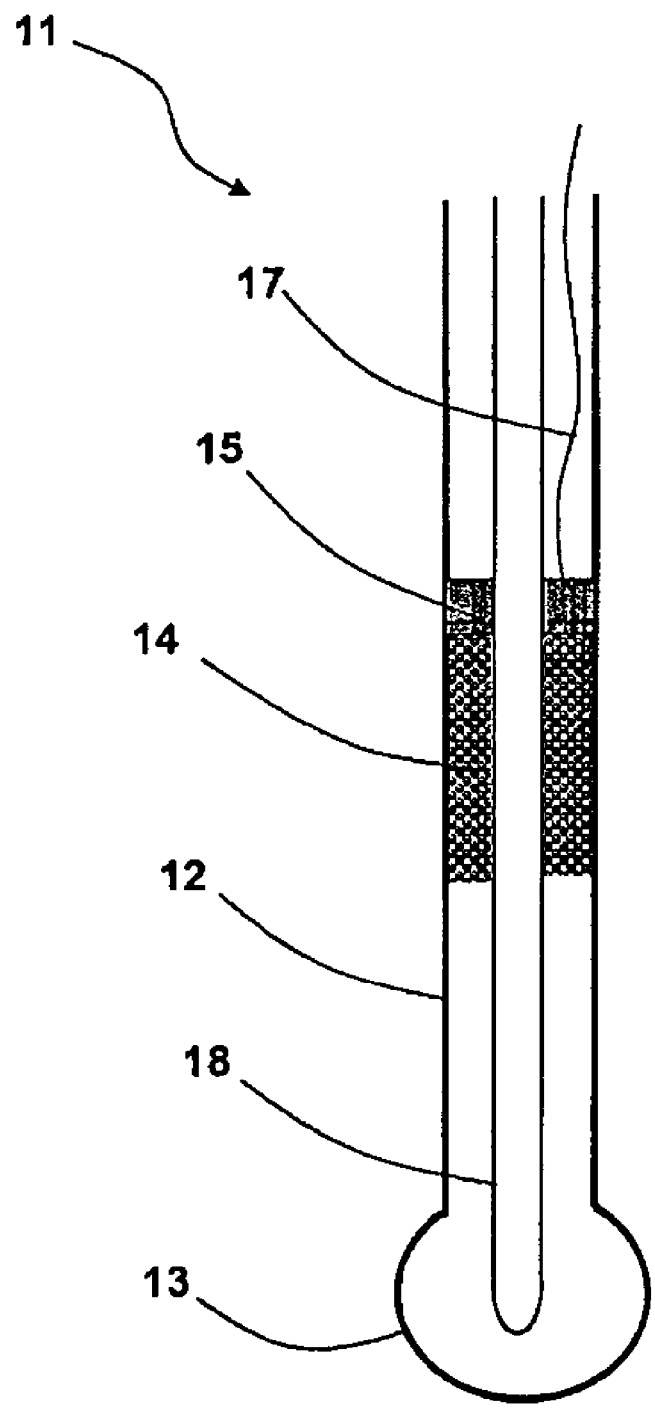
FIG. 2 a longitudinal section through a second example of an embodiment of a pH-electrode of the invention.

The pH-electrode 11 shown in FIG. 2 comprises a cylindrical glass tube 12, whose lower end is closed with a pH glass-membrane 13. The glass tube 12 and the pH glass-membrane 13 surround a volume, which is filled with a KCl-containing pH-buffer.

For forming a pH-dependent potential, a potential-forming element 14 is provided, which comprises an electrically conductive, open-pored and elastic, annular plug, whose pores contain, at least partially, AgCl-particles, which are wetted by the electrolyte, or pH-buffer. The annular plug can comprise, for example, an elastomer made electrically conductively by silver particles, or particles with silver surfaces, wherein the annular plug can be fixed against axial movement by friction created again by radial forces.

The closing element 15 comprises, in this embodiment, an electrically conducting, sealing compound, which comprises an elastomer containing silver particles, which is cast by means of a suited metering apparatus into the glass tube and into electrical contact with the annular plug 14.

For accessing the pH-dependent potential, an end of an electrical current drain wire 17 is cast into the closing element 15, without, however, completely passing through the closing element 15. Optionally, the end of the drain wire can also be adhered to a surface of the closing element, after curing of the elastomer.

Extending along the axis of the pH-electrode is a glass shaft of a temperature sensor 18, which registers the temperature of the pH-buffer about in the center of the volume enclosed by the pH glass-membrane. Due to this temperature sensor, the plug 14 of the potential-forming element and the closing element 15 are embodied to be annularly shaped. When the temperature sensor is absent, instead, a solid stopper is provided for the potential-forming element, and the closing element 15 is accordingly cast completely across the glass tube.

Figure 3:
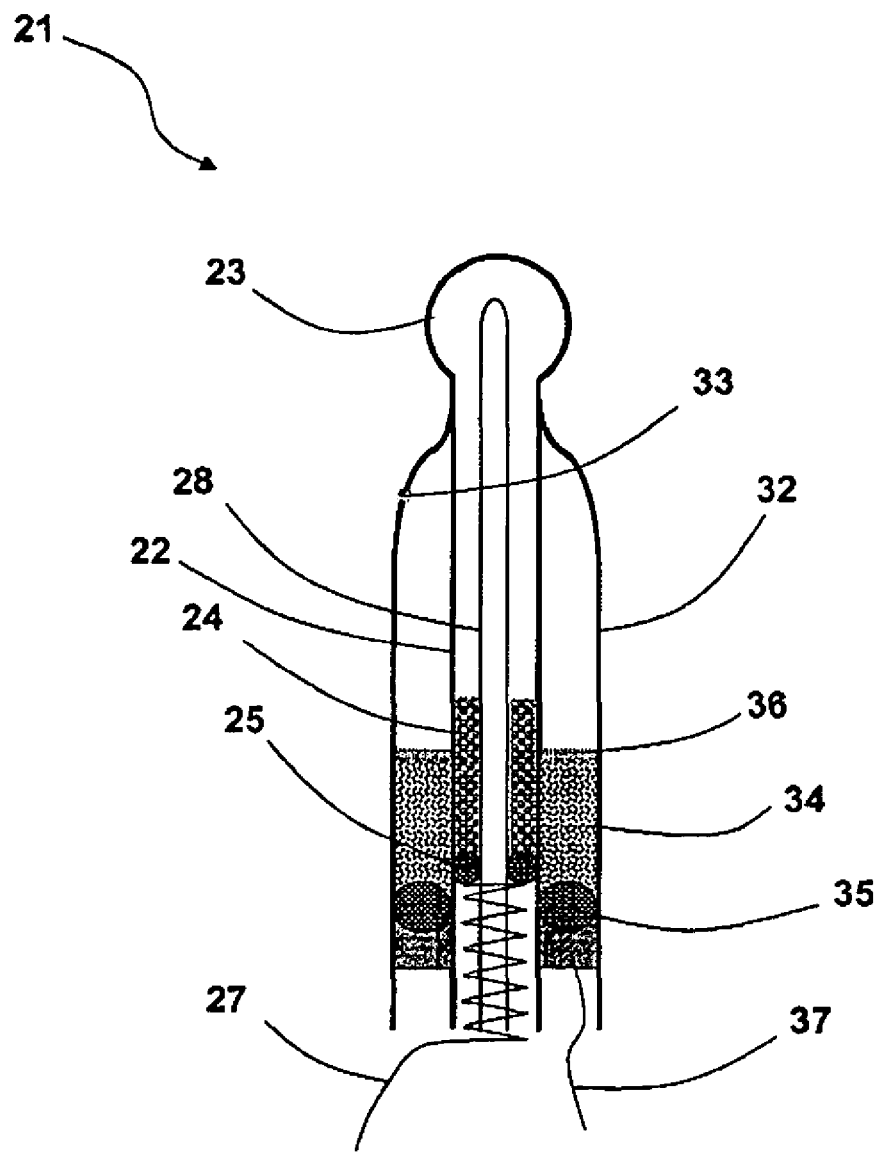
FIG. 3 a longitudinal section through an example of an embodiment of a single-rod measuring chain of the invention.

FIG. 3 shows, finally, a single-rod measuring chain 21 having a pH-electrode of the invention, which is also suited for the inverted mounting, thus, with the pH glass-membrane upwards. In this case, a complete filling of the glass tubes is significantly important for the pH-buffer and for the reference electrolyte, because, in the case of an incomplete filling, for example, the inner wall of the pH glass-membrane would no longer be wetted and the measurement path would, thus, be interrupted.

The pH-electrode of the single-rod measuring chain 21 comprises a cylindrical glass tube 22, whose upper end is closed with a pH glass-membrane 23. The glass tube 22 and the pH glass-membrane 23 surround a volume, which is filled completely with a KCl-containing pH-buffer.

For forming a pH-dependent potential, a potential-forming element 24 is provided, which comprises an electrically conductive, open-pored and elastic, annular plug, whose pores at least partially contain AgCl-particles, which are wetted by the pH-buffer. The annular plug can comprise, for example, an elastomer made electrically conductive by silver particles, or by particles with silver surfaces, wherein the annular plug is axially fixed, for example, frictionally by radial forces.

Bordering the annular plug, in electrically conducting contact therewith, is a closing element 25, which sealedly closes the volume filled with the pH-buffer and the potential-forming element 24.

Closing element 25 comprises, in this embodiment, an electrically conductive O-ring of an elastomer containing silver particles or silver-containing particles. The O-ring is fixed sufficiently against movement in the axial direction by friction resulting from radial forces.

For accessing the pH-dependent potential, the O-ring is contacted via a contact spring 27, which presses against the side of the O-ring facing away from the potential-forming element 24. The contact spring 27 is, in such case, axially pre-compressed to an extent such that an electrical contact remains in the presence of shaking and temperature fluctuations, while, however, the level of compression is limited such that no axial shifting of the O-ring 25 occurs because of the contact spring.

Extending along the axis of the pH-electrode is a glass shaft of a temperature sensor 28, which registers the temperature of the pH-buffer about in the center of the volume enclosed by the pH glass-membrane 23.

The glass tube 22 of the pH-electrode is coaxially surrounded by a second glass tube 32, so that, between the two glass tubes, an annular chamber is formed, which is filled with a reference electrolyte, which comprises a 3 molar KCl-solution.

The second glass tube 32 is, in an axial end section, which adjoins the axial position of the pH glass-membrane, bonded with the glass tube 22 of the pH-electrode by melting, whereby the annular chamber is closed at the end region contactable with a medium to be measured. In this end region, the outer glass tube has, furthermore, a porous ceramic diaphragm 33, through which an electrolyte bridge to, or junction with, the measured medium is implemented.

For forming a reference potential, there is provided in the annular chamber an AgCl-reservoir 34, which comprises silver grains, or grains with a silver surface, especially silvered glass grains, which are at least partially chlorided, and are in electrically conducting contact with a closing element 35, which closes the reference electrolyte filled section of the annular chamber between the first glass tube 22 and the second glass tube 32.

For fixing the axial position of the AgCl-reservoir 34, there is provided in the annular chamber an axial barrier 36, which is porous for the reference electrolyte, so that such can wet the AgCl-reservoir. Barrier 36 can comprise, for example, an annular sieve plate of glass or plastic. The closing element 35 comprises, in this embodiment, an electrically conductive O-ring of an elastomer containing silver particles. The O-ring is sufficiently fixed in the axial direction by friction resulting from radial forces.

For accessing the reference potential, an end section of a drain wire 37 is adhered with a conductive adhesive in electrical contact with the O-ring in the annular chamber, wherein the conductive adhesive can additionally serve as a seal, redundantly to the O-ring.

Although FIG. 3 shows the single-rod measuring chain in an inverted arrangement, this relates only to an advantageous application of the invention, since, of course, the invention includes measuring arrangements with any other orientations of the electrodes.

The invention claimed is:

1. An electrode, comprising:
at least a first, preferably cylindrical, glass body, in which at least a first chamber is formed;
at least a first electrolyte, which is located in said first chamber;
at least a first potential-forming element, which is arranged in said chamber, and forms a first potential when contacted by said first electrolyte;
at least a first closing element, which is axially fixed in said first chamber for enclosing said first electrolyte and said first potential-forming element, and which sealedly closes said first chamber; and
at least a first electrical conductor, which electrically contacts said first closing element on a side of said first closing element facing away from said first electrolyte, wherein:
said first closing element is conductive; and
said first potential-forming element conductingly contacts said first closing element.

2. The electrode as claimed in claim 1, wherein:
said first potential-forming element comprises an AgCl-reservoir, which is wetted by the electrolyte and is in electrically conducting connection with said electrically conductive, closing element.

3. The electrode as claimed in claim 2, wherein:
said first potential-forming element comprises a conductive element body, which comprises a porous elastomer, and which contacts said closing element.

4. The electrode as claimed in claim 3, wherein:
said pores of said conductive element body contain said electrolyte and AgCl.

5. The electrode as claimed in claim 3, wherein:
said elastomer of the element body contains embedded silver particles, silver-containing particles, or glass particles coated with Ag.

6. The electrode as claimed in claim 3, wherein:
said element body is formed as one-piece with said closing body.

7. The electrode as claimed in claim 1, wherein:
said closing element comprises a conductive closing body of elastomer.

8. The electrode as claimed in claim 7, wherein:
the elastomer of said closing body contains embedded silver particles, silver-containing particles, or glass particles coated with Ag.

9. The electrode as claimed in claim 7, wherein:
said closing body is pressed into an opening of said glass body, and said closing element is fixed frictionally in its axial position by radial forces.

10. The electrode as claimed in claim 1, wherein:
said closing element comprises a conductive adhesive.

11. The electrode as claimed in claim 10, wherein:
the adhesive contains embedded silver particles, silver-containing particles, or glass particles coated with Ag.

12. The electrode as claimed in claim 1, wherein:
said electrode is a pH-electrode.

13. The electrode as claimed in claim 12, wherein:
a first axial end of said glass body is closed with a pH glass-membrane to form said first chamber, and said first electrolyte comprises a pH-buffer.

14. The electrode as claimed in claim 1, further comprising:
a reference electrode and a reference electrolyte arranged in said chamber.

15. The electrode as claimed in claim 14, wherein:
said reference electrolyte comprises a KCl-solution.

16. The electrode as claimed in claim 14, further comprising:
a porous diaphragm arranged in an end section of said cylindrical glass body.

17. A single-rod measuring chain, comprising:
a pH-electrode; and
a reference electrode, wherein:
said pH-electrode and said reference electrode each comprise a cylindrical glass body and said glass body of said reference electrode surrounds said glass body of said pH-electrode to form an annular chamber,
said pH-electrode further comprising:
at least a first electrolyte which is located in at least a first chamber formed in said glass body of said pH-electrode;
at least a first potential-forming element, which is arranged in said first chamber, and forms a first potential when contacted by said first electrolyte;
at least a first closing element, which is axially fixed in said first chamber for enclosing said first electrolyte and said first potential-forming element, and which sealedly closes said first chamber; and at least a first electrical conductor, which electrically contacts said first closing element on a side of said first closing element facing away from said first electrolyte, wherein:

said first closing element is conductive; and said first potential-forming element conductingly contacts said first closing element.

18. A single-rod measuring chain, comprising:

a pH-electrode; and a reference electrode, wherein:

said pH-electrode and said reference electrode each comprise a cylindrical glass body and said glass body of said reference electrode surrounds said glass body of said pH-electrode to form an annular chamber, said reference electrode further comprising:

at least a reference electrolyte which is located in said annular chamber;

at least a first potential-forming element, which is arranged in said annular chamber, and forms a first potential when contacted by said reference electrolyte;

at least a first closing element, which is axially fixed in said annular chamber for enclosing said reference electrolyte and said first potential-forming element, and which sealedly closes said annular chamber; and at least a first electrical conductor, which electrically contacts said first closing element on a side of said first closing element facing away from said reference electrolyte, wherein:

said first closing element is conductive; and said first potential-forming element conductingly contacts said first closing element.

19. A single-rod measuring chain, comprising:

a pH-electrode; and a reference electrode, wherein:

said pH-electrode and said reference electrode each comprise a cylindrical glass body and said glass body of said reference electrode surrounds said glass body of said pH-electrode to form an annular chamber, said pH-electrode further comprising:

at least a first electrolyte which is located in at least a first chamber formed in said glass body of said pH-electrode;

at least a first potential-forming element, which is arranged in said first chamber, and forms a first potential when contacted by said first electrolyte;

at least a first closing element, which is axially fixed in said first chamber for enclosing said first electrolyte and said first potential-forming element, and which sealedly closes said first chamber; and at least a first electrical conductor, which electrically contacts said first closing element on a side of said first closing element facing away from said first electrolyte, wherein:

said first closing element is conductive; and said first potential-forming element conductingly contacts said first closing element; and said reference electrode further comprising:

at least a reference electrolyte which is located in said annular chamber;

at least a second potential-forming element, which is arranged in said annular chamber, and forms a second potential when contacted by said reference electrolyte;

at least a second closing element, which is axially fixed in said annular chamber for enclosing said reference electrolyte and said second potential-forming element, and which sealedly closes said annular chamber; and at least a second electrical conductor, which electrically contacts said second closing element on a side of said second closing element facing away from said reference electrolyte, wherein:

said second closing element is conductive; and said second potential-forming element conductingly contacts said second closing element.

* * * * *